United States Patent [19]
Maekawa et al.

[11] 3,931,248
[45] Jan. 6, 1976

[54] REACTIVE HIGH POLYMER COMPOUND

[75] Inventors: Yukio Maekawa; Masato Satomura; Akira Umehara, all of Asaka, Japan

[73] Assignee: Fuji Photo Film Co., Ltd., Minami-ashigara, Japan

[22] Filed: Feb. 4, 1974

[21] Appl. No.: 439,673

[30] Foreign Application Priority Data
Feb. 2, 1973  Japan.................. 48-13511
Feb. 2, 1973  Japan.................. 48-13513

[52] U.S. Cl. .......... 260/347.5; 204/159.17; 117/34; 117/32 R; 96/1.5; 96/1.6; 260/332.2 A; 260/78.4 D; 260/2 EP; 260/88.3 A; 260/88.5; 260/88.7; 260/89.1; 260/89.5 R; 260/89.5 A; 260/89.7; 260/91.1 R; 260/91.5; 260/92.1; 260/92.3; 260/93.5 R; 260/93.7; 260/94.2 R; 260/94.9 R; 204/159.14; 204/159.15; 204/159.16
[51] Int. Cl.² ...................... C07D 307/54
[58] Field of Search...................... 260/332.2, 347.4

[56] References Cited
UNITED STATES PATENTS
2,653,866  9/1953  Mowry et al..................... 260/347.4

*Primary Examiner*—Harry I. Moatz
*Attorney, Agent, or Firm*—Sughrue, Rothwell, Mion, Zinn & Macpeak

[57] ABSTRACT

A high polymer compound containing therein the reactive group represented by the following general formula;

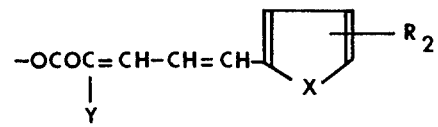

wherein X represents O or S; Y represents a hydrogen atom or a cyano group; and $R_2$ represents a hydrogen atom, an alkyl group having not more than 4 carbon atoms, a halogen atom or a nitro group.

4 Claims, No Drawings

REACTIVE HIGH POLYMER COMPOUND

BACKGROUND OF THE INVENTION

1. Field of the Invention p The present invention relates to a high polymer compound, particularly, to a reactive high polymer compound. More particularly, it is concerned with a high polymer compound which has a skeletal structure which undergoes a reduction in solubility or becomes insoluble due to the action of light, heat, electron beams, particle rays, electromagnetic waves or the like.

2. Description of the Prior Art

Heretofore, many studies have been made on high polymer compounds which undergo a reduction in solubility or become insoluble due to the action of light, heat or electron beams, with respect to relief images, printing plates, resist materials, photographic copies, coating materials, and the like. These are summarized in detail in the literature (e.g., Kosar; *Light-Sensitive Systems*, John Wiley & Sons, New York (1965), and Schonberg; *Preparative Organic Photochemistry*, Springer Verlag, New York (1968), chap.8). Of these, photodimerization-type polymers having cinnamic ester group

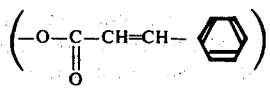

as the light-sensitive group have been well studied (for example, in U.S. Pat. Nos. 2,835,656; 3,357,831; 3,737,319; 3,418,295; 3,647,470; 3,409,593; 2,956,878; 3,173,787; 3,023,100; 3,066,117).

The inventors have previously examined reactive high polymer compounds having a furanacrylic acid ester group known to possess higher sensitivity as compared with the aforesaid cinnamic acid ester group, and like polymer compounds. Furthermore, they have studied reactive high polymer compounds having a thiophenylacrylic acid ester group, and application have been made thereon. As a result of additional studies, the inventors have now developed a reactive high polymer compound with a remarkably high sensitivity, thus achieving the present invention.

SUMMARY OF THE INVENTION

The present invention provides a high polymer compound having as the reactive group in the polymer the group represented by the following general formula;

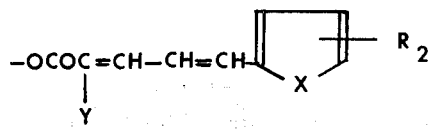

wherein X represents O or S, Y represents a hydrogen atom or a cyano group, $R_2$ represents a hydrogen atom, an alkyl group having not more than 4 carbon atoms (such as methyl, ethyl, propyl, isopropyl, butyl, t-butyl and sec-butyl), a halogen atom (such as achlorine atom, a bromine atom etc.) or a nitro group.

DETAILED DESCRIPTION OF THE INVENTION

The high polymer compound having the reactive group represented by the above-described general formula can be prepared using the following two processes: one being a process of introducing the reactive group into a high polymer; and the other being a process of homopolymerizing a monomer having the reactive group or copolymerizing it with other monomers.

These two processes are described in greater detail below. (1) Process of introducing the reactive group into a high polymer:

1-i. Process of reacting a furylpentadienic acid halide or a thienylpentadienic acid halide with a high polymer compound having a hydroxy group. A suitable molar ratio of the acid halide per hydroxy group containing unit of the polymer (to be esterified), ranges from about 0.1:1 to 10:1, preferably 1:1 to 3:1. In this reaction, catalysts for general esterification reactions, i.e., organic bases (e.g., pyridine, triethylamine, quinoline, diethylaniline, dimethylaniline, methyl piperidine, diazabicyclooctane, triethylene diamine, etc.) or inorganic bases (e.g., sodium hydroxide, potassium hydroxide, sodium carbonate, ionic ion exchange resins, etc.) are effective. A suitable molar ratio of the catalyst per hydroxy group containing unit of the polymer (to be esterified) ranges from about 0.2:1 to 10:1 preferably 1:1 to 3:1. Specific examples of high polymer compounds having a hydroxy group which can be used as the starting material are high polymers such as homopolymers or copolymers of a vinyl or vinylidene monomers having a hydroxy group, such as hydroxyalkyl acrylate, hydroxyalkyl methacrylate, β-chloromethyl-hydroxyethyl methacrylate, hydroxymethylstyrene, hydroxystyrene, etc.; and the like. A furylpentadienic acid chloride and thienylpentadienic acid chloride are preferred acid halides.

In case of a polymer reaction (to obtain a functional group containing polymer starting from a polymer), it is very important to use a homogeneous reaction system, that is, to use a solvent soluble polymer.

Solvent insoluble polymers such as polyvinyl alcohol, and hydroxyethyl cellulose are not convenient starting polymers in case of a polymer reaction.

For example, in U.S. Pat. No. 3,257,664, detailed experimental conditions concerning a reaction of a polymer (polyvinyl alcohol) with an acid chloride are described specifically as follows:

1. In Example 4, a mixture of 22g of polymer and 200 ml of pyridine was heated on a steam bath for 1 hour with stirring and additional 200 ml of pyridine is added before dropwise addition of a melted acid chloride. The reaction is further conducted at 50°C for 4 hours. The yield is about 91 percent.

2. In Example 7, 380 ml of pyridine is used to swell (not to dissolve) 22g of a polymer (polyvinyl alcohol) on a steam bath overnight. After the reaction of the polymer with an acid halide, the reaction mixture is heated at 50°C for 4 hours and diluted with 700 ml of acetone before precipitation in cold water. The resulting polymer is further purified by washing with water 4 times.

In these Examples, the polymer concentration is only 5.5 to 5.8 weight percent to the base (pyridine). Yet, as shown in the specification clearly, the polymer is only swollen by pyridine. That is a heterogeneous, complicated reaction arises from these reaction conditions.

The reaction conditions shown above are very severe, heterogeneous and complicated conditions compared with those of this invention (homogeneous, mild reaction conditions) as will be described later.

The process of this invention is an esterification reaction wherein an acid halide is reacted with a high polymer compound having a hydroxy group. Separately from this process, there is the synthesis of forming an ester bond as follows, which can be employed as the case may be.

1-ii. A process of reacting a high polymer compound having an active halogen atom such as a chlorine atom or a bromine atom (e.g., a homopolymer or a copolymer of chloromethylstyrene, chloroethyl vinyl ether, bischloromethyloxetane, epichlorohydrin, chloropropyl methacrylate, chloroethylacrylate, chloropropylacrylate, vinyl-α-bromoacetate, bromoethyl methacrylate, or the like) with, e.g., furyl (or thienyl) pentadienic acid or a salt thereof sodium furylpentadienate, sodium thienylpentadienate, potassium furylpentadienate, potassium thinylpentadienate, etc. to thereby obtain the ester of the high polymer compound. Examples of catalysts employed in the reaction are triethyl benzyl ammonium chloride, triemethylbenzyl ammonium bromide, tetramethyl ammonium iodide, trimethyl ethyl ammonium iodide, lauryl pyridinium chloride, etc. with the halogen containing unit of the active halogen compound ranging from molar ratio to the ammonium salt of about $10^{-3}:1$ to $10:1$, preferably $5 \times 10^{-3}:1$ to $5 \times 10^{-1}:1$ The process can be suitably conducted at a temperature of $0°$ to $180°C$, preferably $60°$ to $150°C$, for 0.5 to 40 hours, preferably 3 to 10 hours, and in a solvent such as dimethylformamide, diethylformamide, dimethylacetoamide, methylpyrrodidone, hexamethylphosphorylamide, xylene, dioxane, dimethylsulfoxide, dimethoxyethane, phenyl butylether, etc. at a weight ratio of solvent to the polymer of 0.1 to 1000 preferably 5 to 100.

1-iii. a process of reacting a high polymer compound having an epoxy ring (e.g., a homopolymer or copolymer of glycidyl acrylate, p-glycidylstyrene, p-vinylphenyl glycidyl ether, glycidyl methacrylate, butadiene oxide, vinyloxyethylglycidyl ether, methacryloxyethylglycidyl ether, or the like) with, e.g., furyl (or thienyl) pentadienic acid to obtain the ester of the high polymer compound. A suitable molar ratio of the acid to the epoxy group containing unit of the epoxy compound ranges from about 0.2 to 20, preferably 1 to 3, and the process can be conducted at a temperature of about $10°$ to $180°C$, preferably $60°$ to $120°C$ for about 0.2 to 20 hours, preferably 1 to 5 hours. employing dimethylaniline, diethylaniline, dimethylbenzylaniline, diethylbenzylamine, or a hydroxide salt of these materials as a catalyst in a molar ratio of the catalyst to the epoxy group containing unit of the epoxy compound ranging from about $10^{-5}:1$ to $10:1$, preferably $5 \times 10^{-3}:1$ to $5 \times 10^{-1}:1$. Suitable solvents are dimethylformamide, diethylformamide, dimethylacetoamide, methylpyrrolidone, hexamethylphosphorylamide, xylene, dioxane, dimethylsulfoxide, dimethoxyethane, phenylbutylether, etc. at a weight ratio of solvent to the polymer of 0.1:1 to 1000:1 preferably 5:1 to 100:1.

1-iv. a process of utilizing an ester interchange reaction between a high polymer compound of a lower fatty acid ester (e.g., polyvinyl formate, polyvinylacetate, etc.) and, for example, a furyl (or thienyl) pentadienic acid ester to thereby obtain the corresponding ester of the high polymer compound. A suitable molar ratio of the acid ester to the ester group containing unit of the polymer can range from about 0.1:1 to 20:1 preferably 1:1 to 3:1 with the reaction being conducted at a temperature ranging from about $20°$ to $180°C$, preferably $60°$ to $130°C$ for about 0.1 to 20 hours, preferably, 1 to 5 hours.

Suitable ester interchange catalysts are sulfuric acid mercury acetate, tetrabutyltitanate, toluene sulfonic acid etc. employed at a molar ratio of the catalyst to the ester group containing unit of the polymer of about $10^{-3}:1$ to $1:1$, preferably $5 \times 10^{-3}:1$ to $0.5:1$.

Examples of solvent are benzene, toluene, xylene, mesitylene, chlorobenzene, dichlorobenzene, and a weight ratio of the solvent to the polymer ranging from about 1:1 to 1000:1, preferably 2:1 to 50:1 can be employed.

2. A process of homopolymerizing or copolymerizing a monomer having a reactive group:

The monomers having a reactive group can be represented, e.g., by the following general formulae;

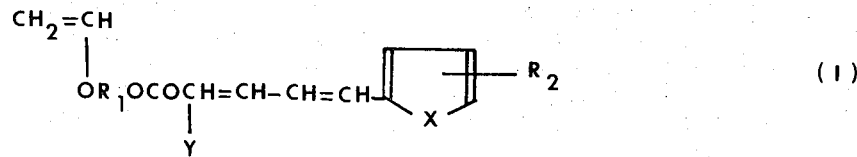 (I)

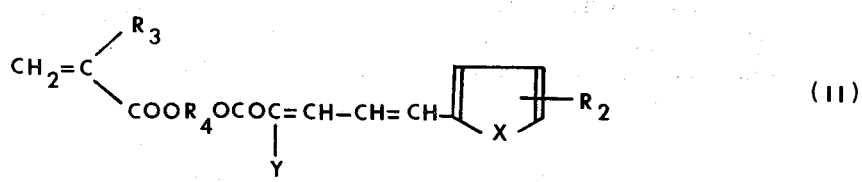 (II)

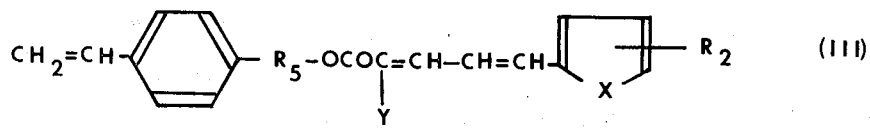 (III)

wherein $R_1$ represents

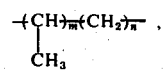,

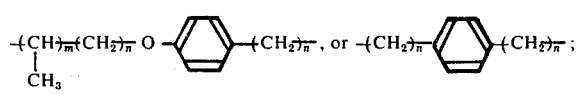, or 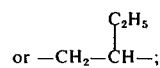;
$R_2$ represents H, $C_nH_{2n+1}$ Cl, Br, F or $NO_2$, $R_3$ represents H or $CH_3$; $R_4$ represents
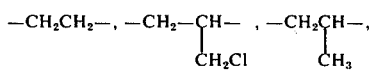
$-CH_2CH-(OCH_2CH_2)_n-$,
or 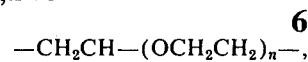;
$R_5$ represents $-(CH_2)_m-$; $m$ represents 0 or 1; $n$ represents an integer of 1 to 4, X represents O or S, and Y represents a hydrogen atom or a cyano group.
Specific examples of the compounds represented by these general formulae are the following compounds
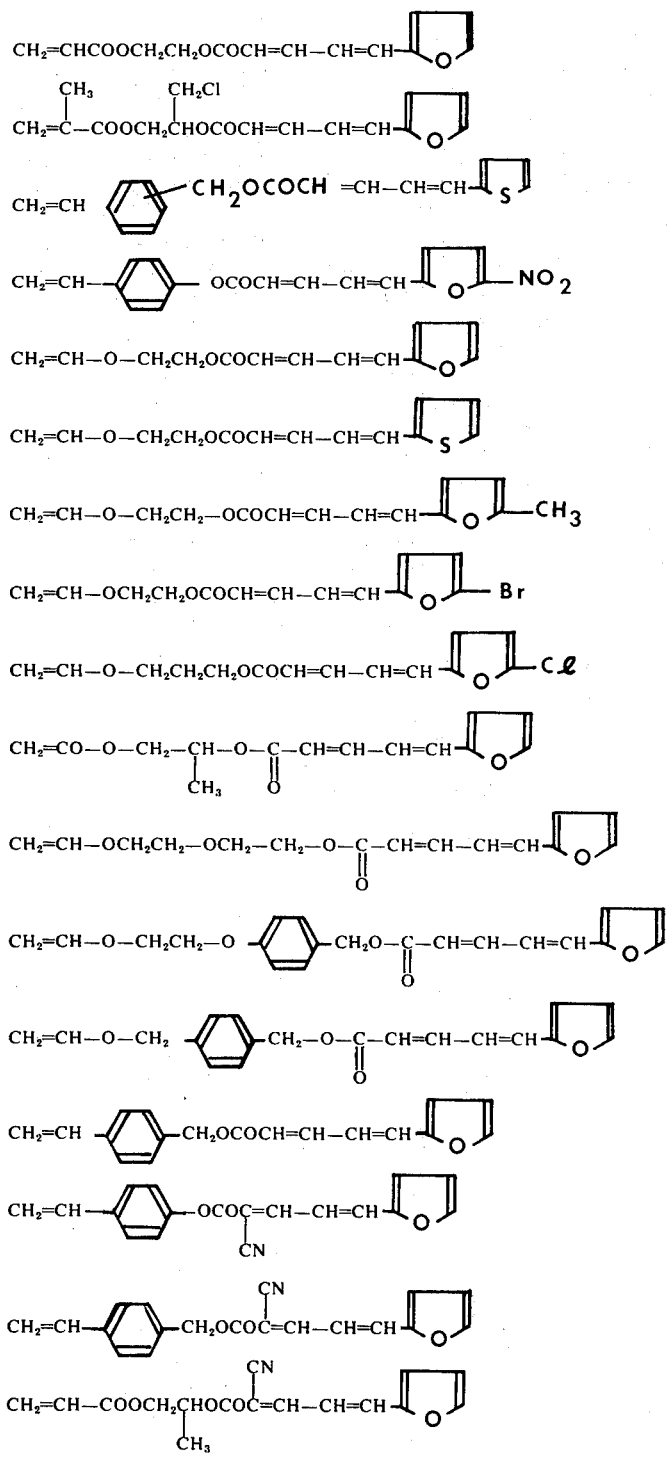

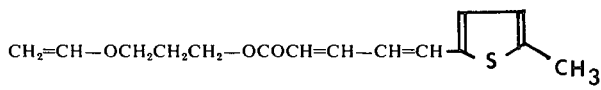
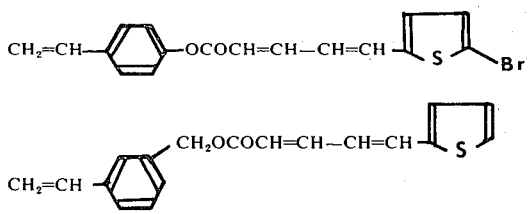

As to the processes for synthesizing these compounds, the following two processes can be employed.

3. A process of reacting a vinyl compound having a haloalkyl group with an alkali metal salt (e.g., sodium, potassium) of an unsubstituted or substituted 5-furyl- or 5-thienyl-2,4-pentadienic acid in the presence of, if necessary, a quaternary ammonium salt catalyst (e.g., triethylbenzyl ammonium chloride, trimethyl benzyl ammonium bromide, tetramethyl ammonium iodide, trimethyl ethyl ammonium iodide, lauryl pyridinium chloride can be used.

A suitable molar ratio of the haloalkyl group containing unit of the haloalkyl group containing polymer compound to the alkali metal salt is about 5:1 to 100:1, preferably 5:1 to 30:1 and a suitable molar ratio of the quaternary ammonium salt to the haloalkyl group containing unit of the polymer compound ranges from about $10^{-3}$:1 to 10:1, preferably $5 \times 10^{-3}$:1 to $5 \times 10^{-1}$:1. Suitable non-solvents which can be used as the reaction medium are dimethylformamide, diethylformamide, dimethylacetamide, methylpyrrodidone, hexamethylphosphorylamide, xylene, dioxane, dimethylsulfoxide, dimethoxyethane, phenylbutylether, etc. at a weight ratio of solvent to the polymer of 0.1:1 to 1000:1, preferably 5:1 to 1000:1.

Suitable vinyl compounds having a haloalkyl group which can be used in Process (3) are the following compounds.

4. A process of reacting a vinyl compound having a hydroxy group with an unsubstituted or substituted 5-furyl- or 5-thienyl-2,4-pentadienic acid halide (e.g., chloride, bromide) in the presence of an organic base (e.g., pyridine, triethylamine, quinoline, diethylaniline, dimethylaniline, methylpiperidine, diazabicyclooctane, triethylene diamine) or inorganic base (e.g., sodium hydroxide, potassium hydroxide, sodium carbonate, ionic ion exchange resins, etc.) can be used.

A suitable molar ratio of the alcohol group of the vinyl compound to the acid haide ranges from about 0.1:1 to 20:1, preferably 0.9:1 to 5:1.

A suitable molar ratio of the catalyst per hydroxy group containing unit of the polymer (to be esterified) ranges from about 0.2 to 10, preferably 1 to 3.

Suitable solvents are benzene, toluene, xylene, ethylether, acetone, tetrahydrofuran, chloroform, methylethyl ketone, methyl acetate, ethylacetate, chlorobenzene, and a suitable weight ratio of the solvent to vinyl compound ranges from about 0.1:1 to 200:1, preferably 1:1 to 10:1 with a reaction temperature ranging from about $-25°$ to $100°C$, preferably $-10°$ to $80°C$, and a reaction time from about 0.1 to 20 hours, preferably 0.5 to 3 hours.

Suitable vinyl compounds having a hydroxy group which can be used in Process (4) are the following compounds.

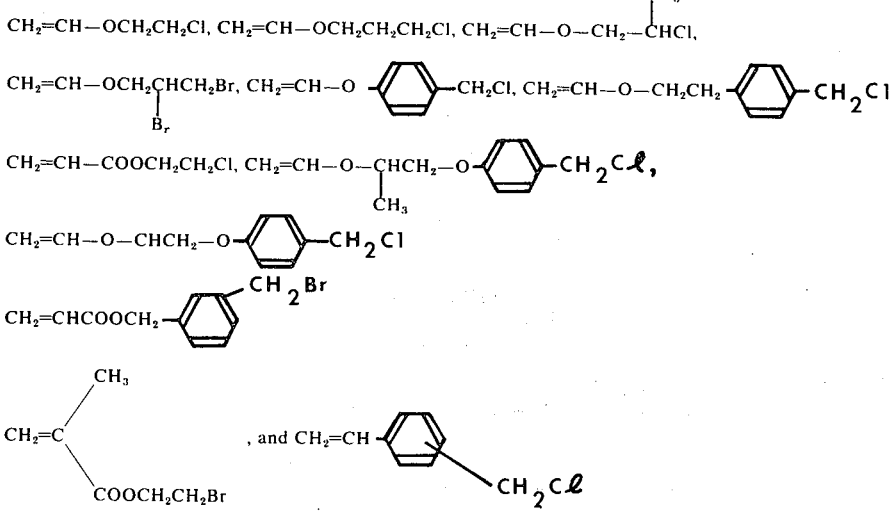

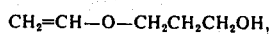
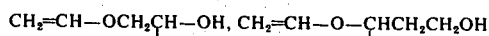
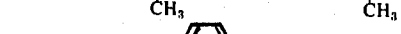
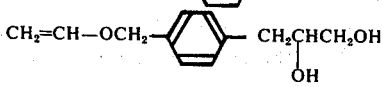
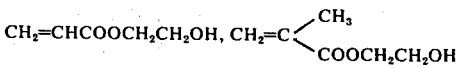
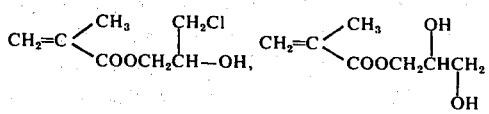
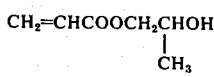
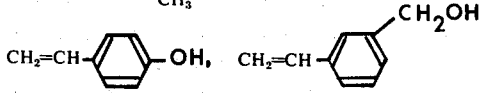

Some of these starting material compounds are described in detail in Murahashi et al; *Synthetic High Polymer III* (1971), Asakura Shoten, Tokyo. Some of them are commercially available.

In the case of copolymerizing these vinyl derivatives having reactive group to thereby obtain a reactive high polymer compound, conventional monomers having an addition-polymerizable group can be used as the comonomer to copolymerize with the vinyl monomers. Examples of such comonomers are, e.g., acrylic esters, acrylamides, methacrylic esters, methacrylamides, allyl compounds, vinyl ethers, vinyl esters, N-vinyl compounds, styrenes, crotonic acid esters, and the like. Specific examples thereof include acrylates such as acrylic acid, an alkyl acrylate (e.g., propyl acrylate, butyl acrylate, amyl acrylate, ethylhexyl acrylate, octyl acrylate, t-octyl acrylate, chloroethyl acrylate, hydroxyethyl acrylate, hydroxypropyl acrylate, 2,2-dimethylhydroxypropyl acrylate, 5-hydroxypentyl acrylate, diethyleneglycol monoacrylate, trimethylolpropane monoacrylate, pentaerythritol monoacrylate, glycidyl acrylate, benzyl acrylate, methoxybenzyl acrylate, furfuryl acrylate, tetrahydrofurfuryl acrylate, etc.), an aryl acrylate (e.g., phenyl acrylate, etc.); methacrylates such as methacrylic acid, an alkyl methacrylate (e.g., methyl methacrylate, ethyl methacrylate, propyl methacrylate, isopropyl methacrylate, amyl methacrylate, hexyl methacrylate, cyclohexyl methacrylate, benzyl methacrylate, chlorobenzyl methacrylate, octyl methacrylate, N-ethyl-N-phenylaminoethyl methacrylate, ethyleneglycol monomethacrylate, 2-hydroxyethyl methacrylate, 3-hydroxypropyl methacrylate, 2-hydroxypropyl methacrylate, 4-hydroxybutyl methacrylate, 5-hydroxypentyl methacrylate, 2,2-dimethyl-3-hydroxypropyl methacrylate, diethyleneglycol monomethacrylate, trimethylolpropane monomethacrylate, pentaerythritol monomethacrylate, glycidyl methacrylate, furfuryl methacrylate, tetrahydrofurfuryl methacrylate, etc.) an aryl methacrylate (e.g., phenyl methacrylate, cresyl methacrylate, naphthyl methacrylate, etc.), etc.; acrylamides such as acrylamide, an N-alkyl acrylamide (the alkyl moiety being, e.g., a methyl group, an ethyl group, a propyl group, a butyl group, a t-butyl group, a heptyl group, an octyl group, a cyclohexyl group, a benzyl group, a hydroxymethyl group, a hydroxyethyl group, a benzyl group, etc.), an N-aryl acrylamide (the aryl moiety being, e.g., a phenyl group, a tolyl group, a nitrophenyl group, a naphthyl group, a hydroxyphenyl group, etc.), an N,N-dialkyl acrylamide (the alkyl moiety being, e.g., a methyl group, an ethyl group, a butyl group, an isobutyl group, an ethylhexyl group, a cyclohexyl group, etc.), N-methyl-N-phenylacrylamide, N-hydroxyethyl-N-methylacrylamide, N-2-acetamidoethyl-N-acetylacrylamide, etc.; methacrylamides such as methacrylamide, an N-alkylmethacrylamide (the alkyl moiety being, e.g., a methyl group, an ethyl group, a t-butyl group, an ethylhexyl group, a hydroxyethyl group, a cyclohexyl group, etc.), an N-arylmethacrylamide (the aryl moiety being, e.g., a phenyl group, etc.), an N,N-dialkylmethacrylamide (the alkyl moiety being, e.g., an ethyl group, a propyl group, a butyl group, etc.), N-hydroxyethyl-N-methylmethacrylamide, N-methyl-N-phenylmethacrylamide, N-ethyl-N-phenylmethacrylamide, etc.; allyl compounds such as an allyl ester (e.g., allyl acetate, allyl caproate, allyl caprylate, allyl laurate, allyl palmitate, allyl stearate, allyl benzoate, allyl acetoacetate, allyl lactate, etc.), allyloxyethanol, etc.; vinyl ethers such as an alkyl vinyl ether (e.g., hexyl vinyl ether, octyl vinyl ether, decyl vinyl ether, ethylhexyl vinyl ether, methoxyethyl vinyl ether, ethoxyethyl vinyl ether, chloroethyl vinyl ether, 1-methyl-2,2-dimethylpropyl vinyl ether, 2-ethylbutyl vinyl ether, hydroxyethyl vinyl ether, diethyleneglycol vinyl ether, dimethylaminoethyl vinyl ether, diethylaminoethyl vinyl ether, butylaminoethyl vinyl ether, phenoxyethyl vinyl ether, tetrahydrofurfuryl vinyl ether, etc.), a vinyl aryl ether (e.g., vinyl phenyl ether, vinyl tolyl ether, vinyl chlorophenyl ether, vinyl 2,4-dichlorophenyl ether, vinyl naphthyl ether, vinyl anthranyl ether, etc.); vinyl esters, such as vinyl acetate, vinyl propionate, vinyl butyrate, vinyl isobutyrate, vinyl trimethylacetate, vinyl diethylacetate, vinyl valerate, vinyl caproate, vinyl chloroacetate, vinyl dichloroacetate, vinyl methoxyacetate, vinyl butoxyacetate, vinyl phenyl acetate, vinyl acetoacetate, vinyl lactate, vinyl β-phenylbutyrate, vinyl cyclohexylcarboxylate, vinyl benzoate, vinyl salicylate vinyl chlorobenzoate, vinyl tetrachlorobenzoate, vinyl naphthoate, etc.; N-vinyl compounds such as N-vinyloxazolidone, N-vinylimidazole, methylvinylimidazole, N-vinylpyrrolidone, N-vinyl-carbazole, N-vinylethylacetamide, etc.; styrenes such as styrene, an alkylstyrene (e.g., methylstyrene, dimethylstyrene, trimethylstyrene, ethylstyrene, diethylstyrene, isopropylstyrene, butylstyrene, hexylstyrene, cyclohexylstyrene, decylstyrene, benzylstyrene, chloromethylstyrene, trifluoromethylstyrene, ethoxymethylstyrene, acetoxymethylstyrene, etc.), an alkoxystyrene (e.g., methoxystyrene, 4-methoxy-3-methylstyrene, dimethoxystyrene, etc.), a halostyrene (e.g., chlorostyrene, dichlorostyrene, trichlorostyrene, tetrachlorostyrene, pentachlorostyrene, bromostyrene, dibromostyrene, iodostyrene, fluorostyrene, trifluorostyrene, 2-bromo-4-trifluoromethylstyrene, 4-fluoro-3-trifluoromethylstyrene, etc.), a carboxystyrene (e.g., vinylbenzoic acid, methyl vinylbenzoate, etc.); crotonic acid esters such as an alkyl crotonate (e.g., butyl crotonate, hexyl crotonate, glycerine monocrotonate, etc.); vinyl chloride; vinylidene chloride; acrylonitrile; butadiene; ethylene; propylene; chloroprene; isoprene; maleic anhydride; and the like.

Of these, an acrylic acid ester, a methacrylic acid ester, a vinyl ether and a styrene derivative are advantageous from the standpoint of reactivity and availability. Also, other monomers having a reactive group, such as β-vinyloxyethyl furylacrylate, β-vinyloxyethyl cinnamate, β-cinnamoyloxyethyl vinyl ether, cinnamoyloxymethylstyrene, β-cinnamoyloxyethyl acrylate and the like, can be used. In addition, in the polymerization of monomers having a reactive group, pigments (such as phthalocyanine, zinc flower, titanium oxide, etc.) can be present. One or more of these monomers can be polymerized provided that the ratio of the monomers reacted is determined so that monomers having the reactive group are contained in the resulting high polymer compound in sufficient amounts for a cross-linking reaction to occur on exposure.

That is, in the polymerization, the ratio should be determined so that a vinyl or vinylidene derivative having a 5-furyl-2,4-pentadienic acid ester group or a 5-thienylpentadienic acid ester group is contained in the resulting copolymer in an amount of not less than 0.2 mol %, preferably not less than 3 mol %.

In obtaining a reactive high polymer using a vinyl monomer as the starting material, suitable catalysts for the polymerization thereof are ionic polymerization catalysts such as Lewis acids or proton acids (e.g., trifluoroborate or the etherate thereof, zinc chloride, diethylzinc, aluminum chloride, triethylaluminum, ethylaluminum dichloride, aluminum isopropoxide, ferric chloride, tin tetrachloride, anhydrous hydrochloric acid, sulfuric acid, trifluoroacetic acid, etc.), or metal sulfates (such as aluminum sulfate, chronium sulfate, iron sulfate, etc.), which can be used alone or in combination. In addition, radical polymerization catalysts such as benzoyl peroxide, azobisisobutyronitrile, potassium persulfate, hydrogen peroxide-sodium sulfite, etc. can also be utilized. These polymerization catalysts are preferably used in an amount of from 0.1 to 10 mol %, preferably 1 to 10 mole %, based on the monomer. Any of the various known processes, such as bulk polymerization, solution polymerization, emulsion polymerization, suspension polymerization and the like, can be applied to the polymerization reaction.

In obtaining a reactive high polymer compound using a vinyl monomer as the starting material, the reaction can be conducted either in the absence of solvent or in a solution. Where a solvent is used, methylene chloride, carbon tetrachloride, toluene, benzene, tetrahydrofuran, methyl ethyl ketone, ethanol, isopropanol, dimethylformamide, methylpyrolidone or a mixture thereof is preferable as the solvent, although the solvent used depends on the kind of the polymerization initiator used.

In conducting the polymerization reaction in a solution, a suitable concentration of the monomer is 1 to 90% (by weight), preferably 30 to 80%. The polymerization can be conducted at $-100°$ to $+150°C$, but preferably it is conducted at $-78°$ to $80°C$. It is advantageous to conduct the polymerization reaction in a solvent since localized heating and localized acceleration of reaction can be prevented.

With the monomers in the present invention, such as furylpentadienic acid alkylvinyl ether, three moieties, i.e., a vinyl moiety, a 1,4-substituted diene moiety and a furan ring moiety, are considered to be reactive. In particular, the furan ring is known to possess cation polymerizability due to its cyclic vinyl ether structure (see, e.g., Murahashi et al; *Gosei Kobunshi(Synthetic High Polymer) III*, Asakura Shoten, Tokyo, 1971.

Therefore, in polymerizing a monomer having a vinyl ether group represented by the general formula (I) using a cationic polymerization catalyst, gellation would be believed to be unavoidable. In fact, however, as shown in Examples, hereinafter a linear polymer soluble in ordinary oganic solvents such as benzene, tetrahydrofuran, etc. can be suprisingly obtained without causing any gellation.

The infrared absorption spectrum of the resulting polymer shows adsorptions at 3130, 1560, 1030, 880 $cm^{-1}$, etc., characteristic of the furan ring, which clearly demonstrates that polymerization has occurred selectively at the vinyl ether group.

The high polymer compound obtained in the present invention has greater light sensitivity as compared with polyvinyl cinnamate, and is useful particularly for a light-sensitive composition.

In particular, the aforesaid process (2) of polymerizing a vinyl monomer to obtain a reactive high polymer compound is very advantageous because the chemical reactivity, solvent property, adhesiveness, photochemical reactivity, film-forming ability, transparency, oleophilicity, hydrophilicity, water-solubility, dyeability, fire retardant property, flexibility or like physical or chemical properties of the end high polymer compound can be broadly and easily changed by suitably selecting the kind and the amount of the comonomer used in the copolymerization.

The present invention will now be illustrated in greater detail by reference the following synthesis examples of the monomer, examples of the polymerization reaction and applications of the resulting high polymer compounds. In all of the examples given herinafter, all parts, percents, ratios and the like are by weight unless otherwise indicated.

SYNTHESIS EXAMPLE OF MONOMER

Synthesis of β-Vinyloxyethyl 5-Furyl-2,4-pentadienate

30 Grams of potassium 5-furyl-2,4-pentadienate, 200 ml of β-chloroethyl vinyl ether and 1.0 g of trimethylbenzylammonium chloride were placed, together with a small amount of a polymerization inhibitor (0.5 g of phenylnaphthylamine), in a 500 ml three-necked flask equipped with a condenser and the reaction was conducted at 110° – 120°C for 5 hours under vigorous stirring. The potassium chloride produced was filtered off and washed with 20 ml of chloroethyl vinyl ether. This washing and the mother liquor were combined and the chloroethyl vinyl ether was distilled off under reduced pressure.

Then, the residue was rectified under reduced pressure to obtain the product as a pale yellow solid. Upon recrystallization from n-hexane, 31 g of white crystals was obtained. Yield: 90%. m.p.:63° – 64°C.

EXAMPLE 1

In a glass polymerization vessel purged with dry argon gas were placed 1.0 g of β-vinyloxyethyl 5-furyl-2,4-pentadienate and 4.0 ml of methylene chloride and, at 0°C, a $4.3 \times 10^{-4}$ mol/ml methylene chloride solution of boron trifluoride etherate was added thereto as a polymerization catalyst in an amount of 4 mol % based on the monomer.

After maintaining the temperature at 0°C for 1 hour, the contents of the polymerization vessel was poured, under stirring, into 150 ml of methanol containing a small amount of ammonia. Thus, the high polymer compound was obtained as a white solid, which was soluble in ordinary organic solvents such as benzene, tetrahydrofuran, methyl ethyl ketone, etc.

The yield of the high polymer compound after drying at room temperature (about 20° – 30°C) in vacuo was 0.18 g. The intrinsic viscosity, [η], measured in tetrahydrofuran at 30°C was 1.67 (dl/g).

EXAMPLE 2

While Example 1 showed an example of a homopolymerization reaction, this Example shows an example of a copolymerization reaction. The same procedures as described in Example 1 were conducted using the following monomers. That is, to a solution of 1.0 g of β-vinyloxyethyl 5-furyl-2,4-pentadienate, 0.5 g of isobutyl vinyl ether and 4.0 ml of methylene chloride was added boron trifluoride etherate (as a $4.3 \times 10^{-4}$ mol/ml methylene chloride solution) in an amount of 4 mol % based on the monomers, and the polymerization reaction was conducted for 2 hours in the same manner as described in Example 1.

The thus obtained high polymer compound was soluble in organic solvents such as benzene, tetrahydrofuran, methyl ethyl ketone, etc. Yield: 1.25 g. The viscosity, [η], measured in tetrahydrofuran at 30°C was 1.25 (dl/g).

The thus synthesized reactive high polymer compound undergoes a reduction in solubility or becomes insoluble due to the action of light, heat, or electron beam.

As to the reaction mechanism giving rise to this phenomenon, the inventors believe that a four-membered ring-forming reaction takes place, although the precise mechanism is not completely clear due to the absolutely novel skeletal structure.

As a result of examining the relative sensitivity of the high polymer compound having the skeletal structure of the present invention according to a gray scale method, it was found that the sensitivity of the high polymer of the present invention was about 10 times that of a commercially available polyvinyl alcohol cinnamic acid ester containing a sensitizer (e.g., polyvinyl alcohol cinnamate, (DP=1700 to 2700) with a sensitizer, 2-benzoyl methylene-N-methyl-β-naphthothiazoline 8 to 10 weight % to the polymer, cinnamic acid ester content up to 98 mole %, as described in U.S. Pat. No. 2,610,120. A light-sensitive composition using a reactive high polymer compound having such high sensitivity is considered to be extremely useful. For example the exposure time can be reduced to 1/10, which is a great advantage, and a reduction in the working time and an improvement in efficiency can be obtained. Thus, the high polymer compound of the present invention is expected to contribute greatly to the industry in this field.

Suitable sensitizing agent which can be used with the photosensitive polymer of this invention are aromatic carbonyl compounds, aromatic nitro compounds, aromatic quinone compounds, or like photographic sensitizing dyes. These are used in a proportion of 1 to 20% (by weight) based on the high polymer compound.

To illustrate representative specific examples of carbonyl compounds, benzoin, benzoin methyl ether, benzophenone, anthraquinone, benzanthrone, 9-anthraldehyde, 9.10-anthraquinone, 2-methylanthraquinone, acetonaphthone, xanthone, tetramethylaminobenzophenone, tetraethylaminobenzophenone, butylanthraquinone, dimethoxythiobenzophenone, 9,10-phenanthrenequinone, diacetyl, benzyl, chloroanthraquinone and the compound represented by the following general formula;

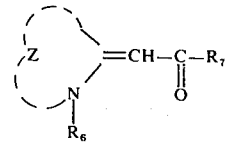

are useful.

In the above general formula, $R_6$ represents an alkyl group conventionally present in cyanine dyes, preferably, an unsubstituted lower alkyl group (e.g., a methyl group, an ethyl group, etc.), a hydroxyalkyl group (e.g., a 2-hydroxyethyl group, etc.), an alkoxyalkyl group (e.g., a 2-methoxyethyl group, etc.), a carboxyalkyl group (e.g., a 2-carboxyethyl group, etc.), a sulfoalkyl group (e.g., a 2-sulfoethyl group, a 3-sulfopropyl group, etc.), an aralkyl group (e.g., a benzyl group, a phenethyl group, a p-sulfophenethyl group, a p-carboxyphenethyl group, etc.), or a vinylmethyl group, $R_7$ represents an alkyl group (preferably a lower alkyl group such as a methyl group, an ethyl group or a propyl group), an aryl group (preferably, a phenyl group, a p-hydroxyphenyl group, a naphthyl group or the like) or a thienyl group, and Z represents the non-metallic atoms necessary to form a heterocyclic nucleus conventionally present in cyanine dyes, such a benzothiazole (e.g., benzothiazole, 5-chlorobenzothiazole, 6-chlorobenzothiazole, 4-methylbenzothiazole, 6-methylbenzothiazole, 5-phenylbenzothiazole 6-methoxybenzothiazole, 4-ethoxybenzothiazole, 5-methoxybenzothiazole, 5-hydroxybenzothiazole, 5,6- dimethylbenzothiazole, 5,6-dimethoxybenzothiazole, etc.), a naphthothiazole (e.g., α-naphthothiazole, β-naphthothiazole, etc.), a benzoselenazole (e.g., benzoselenazole, 5-chlorobenzoselenazole, 6-methylbenzoselenazole, 6-methoxybenzoselenazole, etc.), a naphthoselenazole (e.g., α-naphthoselenazole, β-naphthoselenazole, etc.), a benzoxazole (e.g., benzoxazole, 5-methylbenzoxazole, 5-phenylbenzoxazole, 6-methoxybenzoxazole, etc.), or a naphthoxazole (e.g., α-naphthoxazole, β-naphthoxazole, etc.) nucleus.

Specific examples of compounds represented by the above general formula include, e.g., 2-benzoylmethylene-3-methyl-β-naphthothiazoline, 2-benzoylmethylene-3-ethyl-β-naphthothiazoline, 3-ethyl-2-(2-thenoyl)-methylene-β-naphthothiazoline, 3-ethyl-2-propionylmethylene-β-naphthothiazoline, 5-chloro-3-ethyl-2-p-methoxybenzoylmethylenebenzothiazoline, and the like.

Suitable organic sulfur compounds are di-n-butyldisulfide, di-n-octyldisulfide, dibenzyldisulfide, diphenyldisulfide, dibenzoyldisulfide, diacetyldisulfide, 2-mercaptobenzothiazole, 2-mercaptobenzoxazole, 2-mercaptobenzimidazole, thiophenol, thiocresol, p-methoxybenzenethiol, carboxymethyl-N,N-dimethyldithiocarbamate, ethyl trichloromethanesulfonate, and the like.

As the peroxides, there are hydrogen peroxide, di-t-butyl peroxide, benzoyl peroxide, methyl ethyl ketone peroxide, and the like.

Redox compounds comprise the combination of a peroxide and a reducing agent, and suitable combination are ferrous ion and hydrogen peroxide, ferrous ion and persulfate ion, and ferric ion and a peroxide.

As the azo and diazo compounds, there are α,α-azobisisobutyronitrile, 2-azobis-2-methylbutyronitrile, 1-azo-bis-cyclohexanecarbonitrile, p-aminodiphenylamine diazonium salt, and the like.

Suitable halogen compounds are chloromethylnaphthyl chloride, phenacyl chloride, chloroacetone, β-naphthalenesulfonyl chloride, xylenesulfonyl chloride, and the like.

As the photoreducible dyes, there are Rose Bengal, Erythrosine, Eosine, acriflavine, riboflavine, Thionine, and the like.

Examples of nitro compounds are p-nitrodiphenyl, 5-nitro-2-aminotoluene, 4-nitro-1-aminonaphthalene, 4-nitro-1-acetylaminonaphthalene, picric acid, picramide, dichloronitroaniline, nitroacenaphthene, dinitronaphthalene, trinitrofluorenone, tetranitrocarbazole, dinitrobenzeanthracenedione, dinitrodimethylacetyl-tert-butylbenzene, dinitrostilbene disulfonic acid, trinitronaphthalene, dinitrochalcone, and the like.

Others include methyl-3-ethyl-2-benzothiazolinylidene dithioacetate, 2,6-di(p-ethoxyphenyl)-4-(p-amyloxyphenyl)thiapyrilium perchlorate, and the like. Some of these compounds are described in U.S. Pats. Nos. 2,610,120; 2,670,285; 2,670,285; 2,670,287; 2,690,966; 2,732,301; 2,835,656; 2,956,878; 3,023,100; 3,066,117; 3,173,787; 3,357,831; 3,409,593; 3,418,295; 3,453,110; 3,475,617; 3,561,969; 3,575,929; 3,582,327; 3,647,470; 2,7321,566; and 3,737,319; British Pat. No. 659,197 French Pats. Nos. 1,086,257; 1,089,290; and 1,238,262; and in the literature such as J. Kosar *Light Sensitive Systems*, John Wiley and Sons, New York (1965).

It can be decided through simple try-and-error by those skilled in the art what kind of the compound be selected among these and to what extent it should be added. Generally, a suitable amount if 1 to 20% by weight.

In addition adding a sensitizer to the reactive high polymer compound, a thermal polymerization inhibitor or the like can be added thereto so as to increase stability during storage. Specific examples of such thermal polymerization inhibitors include, e.g., p-methoxyphenol, hydroquinone, alkyl- or aryl-substituted hydroquinone, t-butylcatechol, pyrogallol, cuprous chloride, phenothiazine, phenylnaphthylamine, naphthol, 2,6-di-t-butyl-p-cresol, pyridine, nitrobenzene, dinitrobenzene, p-toluidine, methylene blue, the copper salt of an organic acid (such as copper acetate), and the like. These thermal polymerization inhibitors are preferably incorporated in an amount of 0.0001 to 5 parts by weight based on 100 parts by weight of the polymer. These are added in such amount that cross-linking reaction is not substantially prevented and the storage stability is increased.

In the resin composition can further be incorporated various additives such as coloring agents, plasticizers, resins and the like. As the coloring agent, there are, for example, pigments such as titanium oxide, carbon black, iron oxide, a phthalocyanine pigment, an azo pigment, etc. and dyes such as Methylene Blue, Crystal Violet, Rhodamine B, Fuchsine, Auramine, an azo dye, an anthraquinone dye, etc. The coloring agent is preferably added in an amount of 0.1 to 30 parts by weight (for the pigments) or in an amount of 0.01 to 10 parts by weight (for the dyes) based on 100 parts by weight of the polymer. Suitable plasticizers are phthalic esters such as dimethyl phthalate, diethyl phthalate, dibutyl phthalate, diisobutyl phthalate, dioctyl phthalate, octylcapryl phthalate, dicyclohexyl phthalate, ditridecylphthalate, butylbenzyl phthalate, diisodecyl phthalate, diaryl phthalate, etc.; glycol esters such as dimethylglycol phthalate, ethyl phthalylethyl glycolate, methyl phthalylethyl glycolate, butyl phthalybutyl glycolate, triethyleneglycol dicapryl ester, etc.; phosphoric acid esters such as tricresyl phosphate, triphenyl phosphate, etc.; aliphatic dibasic acid esters such as diisobutyl adipate, dioctyl adipate, dimethyl sebacate, dioctyl azelate, dibutyl maleate, etc.; triethyl citrate; glycerine triacetyl ester; butyl laurate; and the like. In addition, other synthetic high polymers such as polymethyl methacrylate, polyglycidyl acrylate, polystyrenebutadiene, polychloroprene, chlorinated rubber, etc. or an emulsified polymer (latex) can be used in combination.

The compound of the present invention finds application as a coating material, a photographic copy, a printing plate, a resist, a relief image and the like. Of these applications, image formation using the high polymer compound of the invention will be described in detail below.

First, the reactive high polymer compound is dispersed together with, if desired, a stabilizing agent, a plasticizer, a dye, other high polymer compounds, a pigment or a sensitizer, in a ketone solvent, an amide solvent, a cellosolve solvent or a halogenated hydrocarbon in a proportion of 0.1 to 95%, particularly 1 to 45% (by weight). Examples of these solvents include acetone, methyl ethyl ketone, methyl isobutyl ketone, cyclohexanone, diisobutyl ketone, ethyl acetate, butyl acetate, n-amyl acetate, methyl formate, ethyl propionate, dimethyl phthalate, ethyl benzoate, toluene, xylene, benzene, ethylbenzene, carbon tetrachloride, trichloroethylene chloroform, 1,1,1-trichloroethane, chlorobenzene, dichlorobenzene, tetrahydrofuran, anisole, diethyl ether, ethyleneglycol monomethyl ether ethyleneglycol monoethyl ether acetate, dimethylformamide, sulforane, dimethylsulfoxide, methylpyrrolidone, hexamethylphosphoramide or a mixture thereof. The resulting solution is applied to a support such as a plastic film (e.g., a polyethylene terephthalate film, etc.), a metal plate (e.g., a zinc plate, an aluminum plate, etc.), a silicone wafer, glass, or the like using conventional coating method such as dip coating, spinner coating, spray coating, extrusion coating, laminating or vacuum deposition to prepare a light-sensitive layer of 0.1 to 300 microns, particularly 0.5 to 5 microns, in thickness.

After providing thereon, if desired, a transparent protective layer, the desired area is exposed followed by processing with a solvent, if necessary. A suitable source for exposure is a mercury lamp, a high pressure mercury lamp, a carbon arc lamp, a cathode ray tube, a laser beam, a tungsten lamp, a photoflood lamp, an electron beam, ultraviolet rays, a xenon lamp, a chmical lamp, sun light, etc. and a suitable exposure amount is about 1/10,000 sec to 30 min., preferably 1/100 sec to 10 min. Thus, the exposed area remains due to the cross-linking reaction, thereby forming an image.

The present invention will now be illustrated specifically in greater detail by the following examples of the invention of application to image formation, which show applications of the light-sensitive composition, thus facilitating the understanding of the present invention.

However, the uses of the reactive high polymer composition of the present invention are not limited only to these examples.

Application Example 1

A 5% (by weight) methyl ethyl ketone solution was prepared using the high polymer compound obtained in the foregoing Synthesis Example 1. This solution was applied to a surface-processed aluminum plate in a thickness of about 3 microns using a No. 26 coating rod under a safe light, and was allowed to dry at room temperature followed by maintainence at 70°C for 5 minutes to dry it completely. The thus obtained light-sensitive plate was exposed for about 5 seconds through a line image original superposed thereon using a 450 W high pressure mercury lamp spaced at a distance of 28 cm as a light source.

Upon development with methyl ethyl ketone, the exposed area was found to be rendered insoluble in the solvent as a result of cross-linking. This was supported by the fact that, when processed with a usual oily dye, the exposed area alone was colored.

Application Example 2

A 5% (by weight) methyl ethyl ketone solution was prepared using the high polymer compound obtained in Synthesis Example 1. To this was added as a sensitizing agent 5-nitroacenaphthene in an amount of 5% (by weight) based on the high polymer compound and stirred to completely dissolve.

The resulting solution was applied to a surface-processed aluminum plate under a safe light using a No. 26 coating rod and was allowed to dry at room temperature followed by maintainence at 70°C for 5 minutes to dry it completely. The thus obtained light-sensitive plate was irradiated through a line image original superposed thereon using a 450 W high pressure mercury lamp spaced at a distance of 28 cm as a light source.

Upon development with methyl ethyl ketone, the exposed area was found to be rendered insoluble as a result of crosslinking.

Alternatively, when the light-sensitive plate was irradiated for 1 minute through a step wedge (optical wedge) of a step difference of 0.11 to 0.16 superposed thereon using a 450 W high pressure mercury lamp spaced at a distance of 28 cm and processed with methyl ethyl ketone, photoinsolubilization was found to have occurred up to 12th step. In order to obtain the same effect using a commercially available polyvinyl alcohol cinnamic acid ester containing a sensitizer (polyvinyl alcohol (molecular weight about 2,000) esterified with cinnamoyl chloride to about 90 mole % esterification in the presence of pyridine; 2-benzoyl-methylene-N-methyl-$\beta$-naphthothiazoline, 8 to 10% by weight to the polymer, as a sensitizer, with the polymer and sensitize being dissolved in a ethoxyethanol and toluene mixture, at 10 weight %), exposure for about 10 minutes was necessary.

Application Example 3

A 6% (by weight) chlorobenzene solution was prepared using the high polymer compound obtained in Synthesis Example 2. This solution was applied to a surface-processed aluminum plate using dip coating under a safe light, and allowed to dry at room temperature followed by maintainence at 70°C for 5 minutes to dry.

The resulting light-sensitive plate was irradited for 5 seconds through a transparent line image original superposed thereon in the same manner as described in Application Example 1. Upon development with methyl ethyl ketone, the unexposed area was dissolved into the methyl ethyl ketone while the exposed area was rendered insoluble. After drying, a distinct image was found to be formed.

Application Example 4

A 10% (by weight) trichlene solution was prepared using the high polymer compound obtained in Synthesis Example 2. To this was added as a sensitizing dye Michler's ketone in a proportion of 5% (by weight) and stirred to dissolve.

The resulting solution was applied to a surface-processed aluminum plate using a No. 26 coating rod, and allowed to dry at room temperature followed by maintainence at 70°C for 5 minutes to dry.

This light-sensitive material was irradiated for about 1 minute through a step wedge of a step difference of 0.11 – 0.16 using a 450 W high pressure mercury lamp spaced at a distance of 28 cm as a light source. Upon development with methyl ethyl ketone, photoinsolublilization was found to have occurred up to 12th step.

While the invention has been described in detail and with reference to specific embodiments thereof, it will be apparent to one skilled in the art that various changes and modifications can be made therein without departing from the spirit and scope thereof.

What is claimed is:

1. A monomer represented by the following formula;

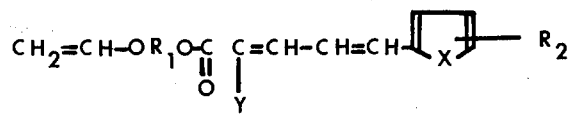

wherein $R_1$ represents

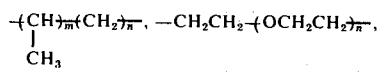, $-CH_2CH_2-(OCH_2CH_2)_n-$,

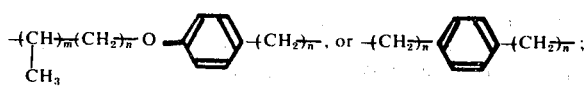

$-CH_2CH_2-$, 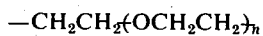

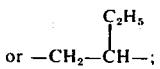

$-CH_2CH_2-(OCH_2CH_2)_n-$ or $-CH_2-\underset{C_2H_5}{\overset{}{CH}}-$;

$R_2$ represents H, $C_nH_{2n+1}$, Cl, Br, F or $NO_2$; X represents O or S; Y represents H or CN; m represents 0 or 1; and n is 1, 2, 3 or 4.

X is O or S; Y is H or CN; n is 1, 2, 3 or 4; and m is 0 or 1.

2. A monomer represented by the following formula:

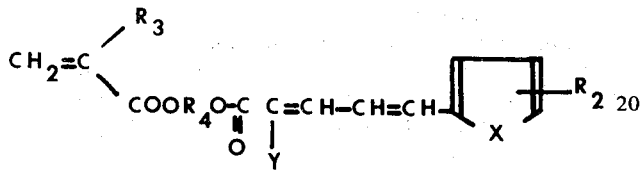

wherein $R_2$ is H, $C_nH_{2n+1}$, Cl, Br, F or $NO_2$; $R_3$ is H or $CH_3$; $R_4$ is 3. A monomer represented by the following formula;

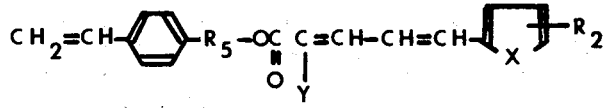

wherein $R_2$ represents H, $C_nH_{2n+1}$, Cl, Br, F or $NO_2$; $R_5$ represents $(CH_2)_m$; X represents O or S; Y represents H or CN; m represents 0 or 1; and n represents 1, 2, 3, or 4.

4. β-vinyloxyethyl-5-furyl-2,4-pentadienate.

* * * * *